(12) United States Patent
Fine et al.

(10) Patent No.: US 8,358,896 B2
(45) Date of Patent: Jan. 22, 2013

(54) FLEXIBLE OPTICAL DEVICE

(75) Inventors: Eran Fine, Tel-Aviv (IL); Noam Meir, Herzlia (IL)

(73) Assignee: Oree, Advanced Illumination Solutions Inc., Ramat-Gan (IL)

(*) Notice: Subject to any disclaimer, the term of this patent is extended or adjusted under 35 U.S.C. 154(b) by 0 days.

(21) Appl. No.: 12/585,591

(22) Filed: Sep. 18, 2009

(65) Prior Publication Data

US 2010/0014822 A1    Jan. 21, 2010

Related U.S. Application Data

(62) Division of application No. 12/219,769, filed on Jul. 28, 2008, which is a division of application No. 10/538,173, filed as application No. PCT/IL03/01042 on Dec. 9, 2003, now Pat. No. 7,639,916.

(60) Provisional application No. 60/431,741, filed on Dec. 9, 2002.

(51) Int. Cl.
  *G02B 6/10* (2006.01)
(52) U.S. Cl. .................................. 385/129; 385/901
(58) Field of Classification Search .................. 385/129
  See application file for complete search history.

(56) References Cited

U.S. PATENT DOCUMENTS

| | | |
|---|---|---|
| 3,261,356 A | 7/1966 | Wallace |
| 3,626,471 A | 12/1971 | Florin |
| 3,871,747 A | 3/1975 | Andrews |
| 3,995,934 A | 12/1976 | Nath |
| 4,551,129 A | 11/1985 | Coleman et al. |
| 4,669,467 A | 6/1987 | Willett et al. |
| 4,783,140 A | 11/1988 | Osawa et al. |
| 4,872,837 A | 10/1989 | Issalene et al. |
| 4,903,172 A | 2/1990 | Schoeniger et al. |
| 5,139,420 A | 8/1992 | Walker |
| 5,152,686 A | 10/1992 | Duggan et al. |
| 5,281,134 A | 1/1994 | Schultz |
| 5,425,730 A | 6/1995 | Luloh |
| 5,535,105 A | 7/1996 | Koenen Meyers et al. |
| 5,559,358 A | 9/1996 | Burns et al. |
| 5,569,254 A | 10/1996 | Carlson et al. |
| 5,580,154 A | 12/1996 | Coulter et al. |
| 5,675,678 A | 10/1997 | Neuberger et al. |
| 5,718,666 A | 2/1998 | Alarcon |
| 5,899,552 A | 5/1999 | Yokoyama et al. |
| 6,097,871 A | 8/2000 | De Dobbelaere et al. |
| 6,278,106 B1 | 8/2001 | Muto et al. |

(Continued)

FOREIGN PATENT DOCUMENTS

| | | |
|---|---|---|
| DE | 19952430 | 5/2001 |
| GB | 2343361 | 5/2000 |

(Continued)

OTHER PUBLICATIONS

Communication Pursuant to Rules 109 and 110 EPC Dated Aug. 10, 2005 From the European Patent Office Re.: Application No. 03778719.9.

(Continued)

*Primary Examiner* — Omar Rojas

(57) ABSTRACT

A flexible and optionally highly elastic waveguide capable of propagating and emitting light is disclosed. The flexible waveguide comprises a flexible material having a surface and an end, wherein a first portion of the light is emitted through at least a portion of the surface of the flexible waveguide, and a second portion of the light is emitted through the end. The flexible waveguide can be used, for example as an area illuminator for many applications. Additionally disclosed is a clothing device for providing illumination. The clothing device comprises clothing (or even optionally a sheet) and a light source for providing light. In one embodiment the clothing device comprises the flexible waveguide.

40 Claims, 12 Drawing Sheets
(6 of 12 Drawing Sheet(s) Filed in Color)

U.S. PATENT DOCUMENTS

| | | | |
|---|---|---|---|
| 6,322,225 | B1 | 11/2001 | Koike |
| 6,408,123 | B1 | 6/2002 | Kuroda et al. |
| 6,488,704 | B1 | 12/2002 | Connelly et al. |
| 6,528,755 | B2 | 3/2003 | Grewell et al. |
| 6,549,709 | B1 | 4/2003 | De Dobbelaere et al. |
| 6,714,711 | B1 | 3/2004 | Lieberman et al. |
| 6,744,960 | B2 | 6/2004 | Pelka |
| 6,754,408 | B2 * | 6/2004 | Toda et al. ............ 385/16 |
| 6,850,665 | B2 | 2/2005 | Grubsky et al. |
| 6,965,709 | B1 | 11/2005 | Weiss |
| 7,068,898 | B2 | 6/2006 | Buretea et al. |
| 7,311,431 | B2 | 12/2007 | Chew et al. |
| 7,433,565 | B2 * | 10/2008 | Joseph et al. ............ 385/128 |
| 7,736,042 | B2 | 6/2010 | Park et al. |
| 7,791,683 | B2 | 9/2010 | Larson et al. |
| 2001/0046142 | A1 | 11/2001 | Van Santen et al. |
| 2002/0122629 | A1 | 9/2002 | Grubsky et al. |
| 2003/0198455 | A1 | 10/2003 | Usami |
| 2004/0196648 | A1 | 10/2004 | Franklin et al. |
| 2006/0245213 | A1 | 11/2006 | Beil et al. |
| 2007/0133935 | A1 | 6/2007 | Fine |
| 2009/0116801 | A1 | 5/2009 | Fine |
| 2009/0161361 | A1 | 6/2009 | Meir et al. |

FOREIGN PATENT DOCUMENTS

| | | |
|---|---|---|
| WO | WO 97/31219 | 8/1997 |
| WO | WO 02/095289 | 11/2002 |
| WO | WO 2004/053531 | 6/2004 |

OTHER PUBLICATIONS

Notice of Allowance Dated May 21, 2009 From the US Patent and Trademark Office Re.: U.S. Appl. No. 10/538,173.
Office Action Dated Dec. 22, 2008 From the Israeli Patent Office Re.: Application No. 169122 and its Translation Into English.
Official Action Dated Aug. 24, 2007 From the US Patent and Trademark Office Re.: U.S. Appl. No. 10/538,173.
Official Action Dated Aug. 24, 2009 From the US Patent and Trademark Office Re.: U.S. Appl. No. 12/219,769.
Official Action Dated Mar. 24, 2008 From the US Patent and Trademark Office Re.: U.S. Appl. No. 10/538,173.
Official Action Dated Jul. 25, 2008 From the US Patent and Trademark Office Re.: U.S. Appl. No. 10/538,173.
Official Action Dated Oct. 29, 2009 From the US Patent and Trademark Office Re.: U.S. Appl. No. 12/219,769.
Official Action Dated Mar. 9, 2010 From the US Patent and Trademark Office Re.: U.S. Appl. No. 12/219,769.
Response Dated Jan. 28, 2010 to Official Action of Oct. 29, 2009 From the US Patent and Trademark Office Re.: U.S. Appl. No. 12/219,769.
Response Dated Jun. 9, 2010 to Official Action of Mar. 9, 2010 From the US Patent and Trademark Office Re.: U.S. Appl. No. 12/219,769.
Response Dated Nov. 4, 2010 to Official Action of Aug. 25, 2010 From the US Patent and Trademark Office Re.: U.S. Appl. No. 12/219,769.
Official Action Dated Jan. 21, 2011 From the US Patent and Trademark Office Re.: U.S. Appl. No. 12/219,769.
Official Action Dated Aug. 25, 2010 From the US Patent and Trademark Office Re.: U.S. Appl. No. 12/219,769.
Official Action Dated Sep. 20, 2010 From the US Patent and Trademark Office Re.: U.S. Appl. No. 12/219,769.
Response Dated Jun. 21, 2011 to Official Action of Jan. 21, 2011 From the US Patent and Trademark Office Re.: U.S. Appl. No. 12/219,769.
Interview Summary Dated Sep. 12, 2011 From the US Patent and Trademark Office Re. U.S. Appl. No. 12/219,769.
Response Dated Oct. 6, 2011 to Official Action of Jul. 7, 2011 From the US Patent and Trademark Office Re.: U.S. Appl. No. 12/219,769.
Official Action Dated Jul. 7, 2011 From the US Patent and Trademark Office Re.: U.S. Appl. No. 12/219,769.
Advisory Action Before the Filing of an Appeal Brief Dated Mar. 20, 2012 From the US Patent and Trademark Office Re.: U.S. Appl. No. 12/219,769.
Official Action Dated Jan. 4, 2012 From the US Patent and Trademark Office Re.: U.S. Appl. No. 12/219,769.
Official Action Dated Feb. 10, 2009 From the US Patent and Trademark Office Re.: U.S. Appl. No. 10/538,173.
Singh et al. "Liquid Crystals: Fundamentals", Worl Scientific, Chap. 1: 1-23, 2002.
Official Action Dated Jun. 7, 2011 From the US Patent and Trademark Office Re.: U.S. Appl. No. 12/324,540.
Official Action Dated May 23, 2012 From the US Patent and Trademark Office Re.: U.S. Appl. No. 12/219,769.

* cited by examiner

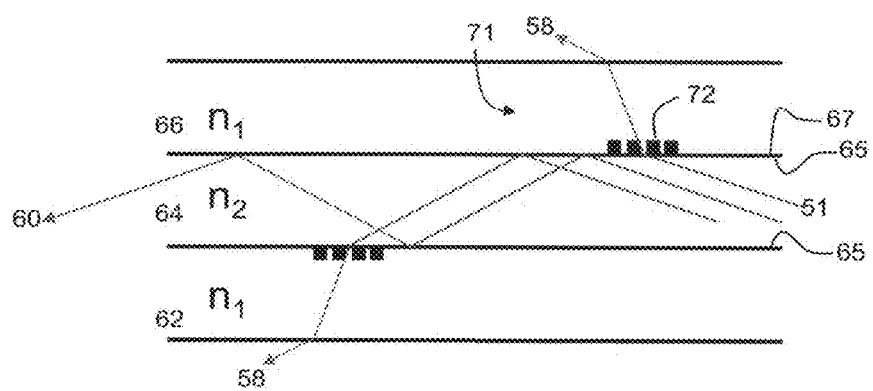
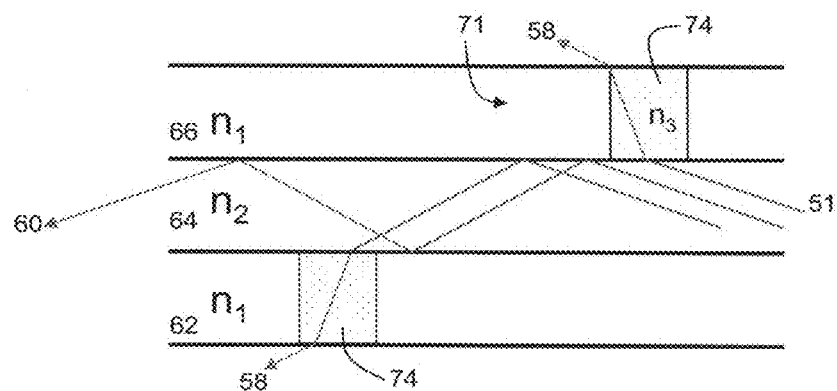

FLEXIBLE OPTICAL DEVICE

RELATED APPLICATIONS

This application is a Divisional of U.S. patent application Ser. No. 12/219,769, filed on Jul. 28, 2008, which is a Divisional of U.S. patent application Ser. No. 10/538,173, filed on Aug. 7, 2006, which is a National Phase Application of PCT/IL03/01042 having International Filing Date of Dec. 9, 2003, which claims the benefit of U.S. Provisional Patent Application No. 60/431,741 filed on Dec. 9, 2002. The contents of the above applications are incorporated herein by reference.

FIELD OF THE INVENTION

The present invention is of a flexible waveguide and its applications, and more particularly, a device and system for directing light to illuminate an area.

BACKGROUND OF THE INVENTION

Illumination devices are useful in many areas of modern life, such as illumination of working area, illumination for the purpose of signaling and illumination carrying different type of information, such as an image and the like.

In medical applications, the requirement for good illumination while operating, both in the operating room (OR) and in emergency and pre-hospital situations is one of the most critical elements of successful surgery and treatment. Until now, lighting techniques in have evolved around the use of strong ceiling and head mounted light fixtures. Even while using minimal invasive techniques, illumination and good access for light source are a critical element is the treatment's success.

Unfortunately, the physical bodies of the surgeons, doctors, paramedics, nurses and devices tend to block light when delivered from ceiling mounted light fixtures, both reducing the overall amount of light available, and producing confusing shadows. Head mounted light fixtures, on the other hand, may provide more directed light which avoids some of the problems of ceiling fixtures, but create other problems, such as strain on the head and neck of the surgeon or nurse wearing such a light.

Hand-held lights, typically held by a nurse, may also be used, but result in other problems, such as the requirement for a nurse or other medical personnel to hold and operate the light, and the necessarily limited size and weight of such lights. Also, this light is directed to the place the surgeon is looking at, not to the place where it is needed. Also, for all such lights, there is a problem of the difference in the quantity of light provided between an area that may be lighted by a hand-held or other light, and areas that do not receive light. This contrast or difference further increases the need for a supplemental light to reduce the differences.

Of course, all of these different types of lighting are best suited for OR and/or emergency room use in controlled hospital settings. Yet even in such an environment, such lighting cannot always provide sufficient illumination for a cavity. This is because of obstacles such as the required angle of incidence and/or various structures that may block the light such as the organs or tissue of the patient as well as the surgeon's hands.

Emergency and/or surgical medicine in some applications, such as military environments for example or pre-hospital situations (trauma center, field medicine, airborne evacuation) provides an even greater challenge as it must be performed under less than optimal medical conditions. These different types of lighting are not always suited for such conditions.

One attempt to overcome this problem has been to combine a cannula, which is a surgical tool, and a light-source. For example, Carlson et al. in U.S. Pat. No. 5,569,254 claim a surgical resection tool with irrigation, lighting, suction and vision. However, it is not disposable and light is conducted through a dedicated optical fiber.

In U.S. Pat. No. 5,425,730, Luloh describes a special cannula for eye surgery that has a plurality of optical fibers running outside said cannula externally.

Berkowitz et al. in U.S. Pat. No. 4,551,129 claim a technique and apparatus for microsurgery including lighter-irrigator hypodermic tube. Light is conducted through optical fibers.

In U.S. Pat. No. 3,626,471 Florin designed a suction/washing unit for brain surgery that is comprised of two tubes having a fiber optic light-source at their front-end.

A suction and illumination device is described in U.S. Pat. No. 3,261,356 by Wallace, in which light is provided through optical fibers located between two concentric tubes.

Schultz in U.S. Pat. No. 5,281,134 provides light to various dental instruments by means of a single continuous optical fiber.

U.S. Pat. No. 5,152,686 to Duggan and Jennings describes a dental appliance that includes a bite block and a suction tube attachment. A fiber optic light source is slidably and removably secured within the bite block.

U.S. Pat. No. 5,139,420 to Walker claims a dental mirror system having a fluid conduit and/or a suction unit and a light transmitting cable to illuminate the work area.

U.S. Pat. No. 3,995,934 to Nath describes a flexible light guide of the liquid filled type. The liquid is contained in a flexible plastic tube. An infrared light is guided through the liquid within a living body for medical applications.

U.S. Pat. No. 5,580,154 to Coulter et al. discloses a glove apparatus including a glove member treated with an illuminative substance having phosphorescence or fluorescent illuminative properties, and a light circuit system integrally packaged therewith. Light from the light circuit system is contained within a ring-like light housing member which is preferably mounted on a finger section of the glove member. The outer glove surface may be decorated to ornately represent a fictional cartoon character, when the glove is implemented as a toy item.

WO 97/31219 to Trow discloses a work or surgical glove and illuminator assembly which includes an illuminator oriented to project a light beam distally of the glove toward the work surface. The illuminator may have a self-contained light source, or utilize fiber optic-transmitted light from a remote light source. The illuminator may be disposed within the interior of the glove and projects a beam of light through a glove tip which is translucent or transparent. The assembly is useful when examining or operating upon an anatomical part of a patient.

GB 2343361 to Spooner discloses a glove, particularly for cyclists, designed to give an illuminated signal so that other road users are made aware of the cyclist's presence. The glove includes an electric light, an electric battery and two electrical contacts arranged to be touched together to switch the light on by completing an electrical circuit between the battery and the electric light. In use, the wearer of the glove brings his thumb and forefinger together so that the two electrical contacts touch and the electric light is illuminated.

U.S. Pat. No. 5,535,105 to Koenen relates to a glove which has a source of illumination mounted on the glove itself, for projecting light through a glove tip.

German Patent No. DE 19952430 is also of interest as background art.

In all aforementioned patents, there is a source of illumination mounted on the glove or other device, but not incorporated within the glove. It should be noted that some of these patents indicate non-medical uses for the glove or other device, as such devices clearly have a broad range of possible applications, including but also extending beyond medical applications.

Issalene and Lantrua in U.S. Pat. No. 4,872,837 claim a surgical or dental instrument and cannulae for aspirating, cleaning, drying and illuminating. A light source is placed in a housing behind a sleeve. The cannula is shaped and positioned for the light generated by the light source to be conveyed in the sleeve then in the cannula, whose wall performs the role of a light guide. Light is conducted axially to the cannula's open end where it emerges out. In one of the embodiments, the cannula tip has a circular bead that improves light distribution at the cannula's tip. However, the cannula's front tip, that is the only light emitting zone, provides a very limited illuminated area. Furthermore, the cannula's tip may be very close to or even in contact with soft tissues that may block the light.

Such "tip-only" illuminating cannulae provide a limited illumination area. In many medical procedures it is advantageous to have a much larger area being illuminated and seen clearly. Also, cannulae in general can only provide light in a limited area near the cannula itself, regardless of the overall area being illuminated. This is a clear disadvantage, because the functions of the cannula may require it to be located at a distance from the area which must be illuminated for the surgeon and/or other medical personnel. Also, a cannula may not always be present.

Furthermore, such cannula are clearly only useful for surgical procedures. A more advantageous lighting device and system would provide directed light for many different types of procedures and environments, including non-medical environments.

SUMMARY OF THE INVENTION

The background art does not teach or suggest a flexible optical device capable of guiding a light while, at the same time, emitting a portion thereof through a predetermined region of its surface area. The background art also does not teach or suggest such a flexible optical device which is useful for a variety of different applications in which the emitted light can be used for illuminating a sufficiently large area. The background art also does not teach or suggest such a flexible optical device in which the emitted light constitutes readable information, such as, but not limited to, an image.

The background art does not teach or suggest a lighting device and system which provides light for manual procedures in the area that such light is needed by the individual performing the procedure. The background art also does not teach or suggest such a lighting device and system whose function can be integrated automatically into the performance of the procedure. The background art also does not teach or suggest such a lighting device and system which is useful for a variety of different environments and procedures, including medical and non-medical procedures.

The present invention overcomes these deficiencies of the background art by providing a flexible waveguide capable of propagating and emitting light. The waveguide comprises a flexible material having a surface and an end, wherein a first portion of the light is emitted through at least a portion of the surface of the flexible waveguide, and a second portion of the light is emitted through the end. The flexible waveguide is preferably elastic, as described in greater detail below.

According to further features in preferred embodiments of the invention described below, the flexible material comprises two or more layers, such that one layer has a refractive index which is larger than the other layer(s), to allow propagation of light via total internal reflection. One layer preferably comprises at least one impurity, capable of scattering the first portion of the light to thereby emit the light through the surface. Alternatively, or additionally, one layer comprises at least one diffractive optical element for diffracting the first portion of the light to thereby emit the first portion through the surface. Still alternatively, one layer includes one or more regions of high refractive index, so as to prevent the light from being reflected.

The present invention overcomes the above deficiencies of the background art by providing a device and system for illuminating a work area in which an individual is performing at least one manual procedure. The device and system of the present invention are preferably implemented as wearable clothing, such as, but not limited to, gloves, sleeves, gowns, coats, protection clothing, hats, socks, which are naturally worn for many different types of manual procedures, in order to protect the individual performing the procedure and/or the environment in which the procedure is being performed. Alternatively, the device of the present invention may also be held by the user, for example, when the device is implemented as an endoscope or another device which is naturally held by the user for performing other tasks. Optionally and preferably, device features the flexible waveguide of the present invention, such that light at a desired wavelength and intensity is emitted therefrom while the individual is performing the procedure.

According to a preferred embodiment of the present invention the flexible optical device is embedded within the material of the clothing during manufacturing process. Alternatively, the flexible optical device may be provided as a separate external layer to the clothing. The flexible optical device preferably includes material for directing the light to a particular point, or, more preferably, multiple points (e.g., an area), in order to avoid absorption of the light by the clothing material before light is provided from the desired location for the purposes of illumination.

The present invention can be implemented in many environments and/or procedures, including, for example, medical environments and/or procedures, in which gloves are the favored clothing. Such medical environments includes those located in a hospital or other controlled medical setting, and those performed in such non or less controlled settings as battlefields or other military or pre-hospital environments, and/or industrial environments. Other examples include, without limitation, "clean rooms" for the production of specialized electronic equipment; law enforcement situations; and scientific and/or research environments.

Additionally, the clothing can be used as an identification device in which the individual who wears the clothing is identified by the wavelength of the light emitted thereby. In particular, when the wavelength of the emitted light is in the invisible range (e.g., infrared or ultraviolet) the individual who wears the clothing, according to a preferred embodiment of the present invention, can not be identified by an unarmed eye.

The clothing according to the present invention optionally and preferably include an external or internal light source connected to the clothing itself, for example through optical fibers being connected to the clothing via a special connector implemented within, or affixed to, the clothing. The light source may optionally be located at a distance from the clothing, for example as a "belt pack" or other portable system for being carried on the body of the person wearing the clothing. Such a "belt pack" may also optionally hold the energy source for the light. Alternatively, the light source may optionally be attached directly to the clothing.

Also, optionally and more preferably, the light is transmitted from various points in the clothing. Optionally, the light is only transmitted from a predetermined region of the clothing, for example, when the clothing is embodied as a glove, the light may be emitted (i) from the entire area of the glove; (ii) from one or more limited areas, e.g., the underside (palm side) of the glove, in order to avoid light being transmitted to the eyes of the user, thereby causing glare; or (iii) from a more specific region, such as, but not limited to, the tips of one or more fingers.

Optionally and more preferably, a plurality of individuals using the clothing for collectively performing a process may wear different types of clothing. For example, a surgeon may optionally choose to wear gloves with illumination at the tips, while a nurse may optionally wear gloves providing illumination over a large portion of the area of the hand.

According to another optional embodiment of the present invention, light emitted from the flexible waveguide preferably provides information, such as a predetermined pattern. For example, the flexible waveguide may emit light of different wavelengths from different regions. This embodiment is particularly useful when the flexible waveguide of the present invention is used for signaling or for displaying predetermined patterns. For example, the flexible waveguide may emit light in one geometrical pattern in one situation and light in another geometrical pattern in a different situation, thereby to serve as a display or to signal the user for a change in the situation (e.g., temperature change).

The present invention may alternatively be embodied as a cannula and/or other surgical instrument, as described in greater detail below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Hereinafter, the term "connected to" also includes "embedded within."

Hereinafter, the term "metallic" includes a material having at least one physical, chemical or optical property of a metal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings, wherein:

FIG. 3c is a schematic illustration of the flexible material in an embodiment in which one layer thereof is formed with one or more diffractive optical elements for at least partially diffracting the light;

FIG. 3d is a schematic illustration of the flexible material in an embodiment in which one or more regions have different indices of refraction so as to prevent the light from being reflected;

DESCRIPTION OF THE PREFERRED EMBODIMENTS

Figure 1:
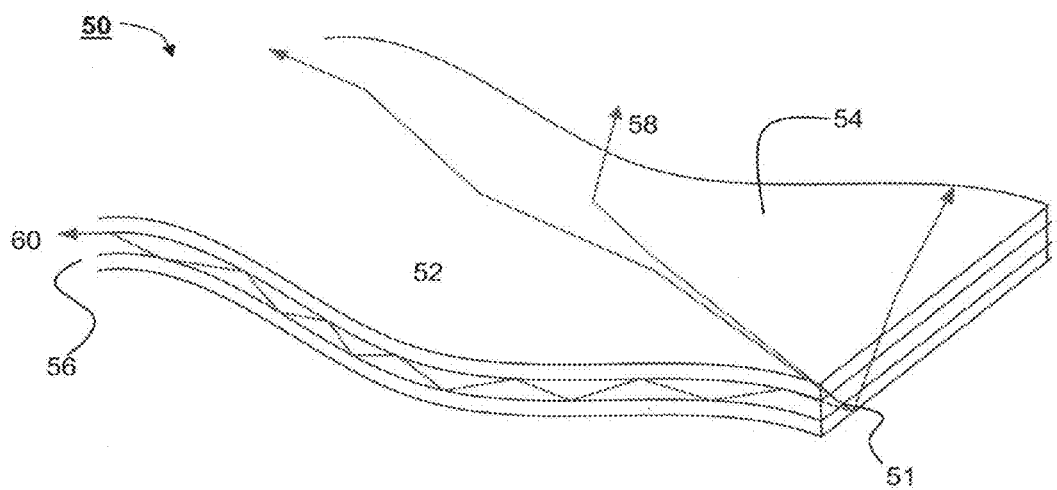
FIG. 1 is a schematic illustration of a waveguide, according to a preferred embodiment of the present invention.

The present invention is of a flexible waveguide which can be implemented, for example, in a device or a system for providing illumination of an area, optionally for performing one or more physical, manual operations. The present invention also preferably includes a device and system for illuminating a work area in which an individual is performing at least one manual procedure.

As the present invention relies upon the ability to transmit and emit light through a waveguide, a brief description of such technology is provided herein. The technology to transmit and guide light rays through optical systems exploits a physical phenomenon known as total internal reflection, in which a light is confined within a material surrounded by other materials with lower refractive index. For the purpose of providing a complete document, the total internal reflection phenomenon is now described herein.

When a ray of light moves within a transparent substrate and strikes one of its internal surfaces at a certain angle, the ray of light can be either reflected from the surface or refracted out of the surface into the open air in contact with the substrate. The condition according to which the light is reflected or refracted is determined by Snell's law, which is a mathematical relation between the impinging angle, the refracting angle (in case in case of refraction) and the refractive indices of both the substrate and the air. Broadly speaking, depending on the wavelength of the light, for a sufficiently large impinging angle (also known as the critical angle) no refraction can occur and the energy of the light is trapped within the substrate. In other words, the light is reflected from the internal surface as if from a mirror. Under these conditions, total internal reflection is said to take place.

Many optical systems operate according to the total internal reflection phenomenon. One such optical system is the optical fiber. Optical fibers are transparent flexible rods of glass or plastic, basically composed of a core and cladding. The core is the inner part of the fiber, through which light is guided, while the cladding surrounds it completely. The refractive index of the core is higher than that of the cladding, so that light in the core impinging the boundary with the cladding at a critical angle is confined in the core by total internal reflection.

As stated, total internal reflection occurs only for light rays impinging the internal surface of the optical fiber with an angle which is larger than the critical angle. Thus, a calculation performed according to geometrical optics may provide the largest angle which is allowed for total internal reflection to take place. An important parameter of every optical fiber (or any other light transmitting optical system) is known as the "numerical aperture," which is defined as the sine of the largest incident light ray angle that is successfully transmitted through the optical fiber, multiplied by the index of refraction of the medium from which the light ray enters the optical fiber.

Another optical system designed for guiding light is the graded-index optical fiber, in which the light ray is guided by refraction rather than by total internal reflection. In this optical fiber, the refractive index decreases gradually from the center outwards along the radial direction, and finally drops to the same value as the cladding at the edge of the core. As the refractive index does not change abruptly at the boundary between the core and the cladding, there is no total internal reflection. However, although no total internal reflection takes place, the refraction bends the guided light rays back into the center of the core while the light passes through layers with lower refractive indexes.

Optical fibers are available in various lengths and core-diameters. For large core diameters, glass optical fibers are known to be more brittle and fragile than plastic optical fiber.

Another type of optical system is based on photonic materials, where the light ray is confined within a band gap material surrounding the light ray. In this type of optical system, also known as a photonic material waveguide, the light is confined in the vicinity of low-index region. One example of a photonic material waveguide is a silica fiber having an array of small air holes throughout its length. This configuration is capable of providing lossless light transmitting, e.g., in either cylindrical or planar type waveguides.

The above description holds both for polarized and unpolarized light. When polarized light is used, an additional electromagnetic phenomenon influences the reflection of the light, as further explained hereinbelow.

Polarized light is produced when the direction of the electromagnetic fields in the plane perpendicular to the direction of propagation are constrained in some fashion. For the purpose of providing a simple explanation, only the electric field is discussed herein. A complementary explanation, regarding the magnetic field, can be easily obtained by one ordinarily skilled in the art by considering the magnetic field as being perpendicular to both the direction of propagation and the electric field.

The light is said to be elliptically polarized when two perpendicular components of the electric field have a constant phase difference, and the tip of the electric field vector traces out an ellipse in the plane perpendicular to the direction of propagation. Linearly polarized light is a special case of elliptically polarized light, where the two components oscillate in phase and the electric vector traces out a straight line.

Circularly polarized light is also a special case of elliptically polarized light in which the two components have a 90° phase difference and the electric field vector traces out a circle in the plane perpendicular to the direction of propagation. When viewed looking towards the source, a right circularly polarized beam at a fixed position as a function of time has a field vector that describes a clockwise circle, while left circularly polarized light has a field vector that describes a counter-clockwise circle.

When polarized light strikes a surface between two different materials, it is useful to define the polarization of the light relative to the surface, typically horizontal and vertical polarizations, with respect to the surface. When the light strikes a material having associated values of permeability, permittivity and conductivity, a portion of the energy carried by the light is lost due non-ideal conductivity of the material. The relative portion of the energy which is lost is defined as the reflection coefficient of the material. The reflective coefficient varies according to the angle of incidence, the polarization of the incoming wave, its frequency and the characteristics of the surface. For horizontal polarizations the coefficient may be generalized to a constant value, whereas for vertical polarizations however, the coefficient varies between 0 and 1.

When the reflective coefficient value goes to zero, the light is not reflected from the surface. This phenomenon is known as the Brewster effect, and the angle at which there is not reflection (for a particular polarization) is called the Brewster angle. This angle often referred to as the polarizing angle, since an unpolarized wave incident on an interface at this angle is reflected as a polarized wave with its electric vector being perpendicular to the plane of incidence.

The present invention provides a waveguide which can be used for providing illumination of a working area. As further detailed hereinunder, there are two physical phenomena (in addition to total internal reflection) which may be exploited by the waveguide of the present invention. These are scattering and diffraction of light.

Unlike the above mentioned reflection, where radiation is deflected from the surface in one direction, some particles and molecules, also known as scatterers, have the ability to scatter radiation in more than one direction. Many types of scatterers are known. Broadly speaking, scatterers may be categorized into two groups: (i) selective scatterers, which are more effective at scattering a particular wavelength (i.e., color), or a narrow range of wavelengths, of the light; and (ii) non-selective scatterers are capable of scattering light in a wide range of wavelengths.

The diffraction phenomenon is the slight bending of light as it passes around the edge of an object, or at an opening thereof. The amount of bending depends on the relative size of the wavelength of light to the size of the opening. If the opening is much larger than the light's wavelength, the bending will be almost unnoticeable. However, if the two are closer in size or equal, the amount of bending is considerable, and easily seen with the naked eye. Light can also be diffracted when passing between two close particles, when the physical separation between the particles is of the order of the light's wavelength.

Optical effects resulting from diffraction are produced through the interaction of light waves originating from different regions of the opening causing the diffraction. Illustratively, one can view this interaction as one of two types of interferences: (i) a constructive interference when the crests of two waves combine to produce an amplified wave; and (ii) a destructive interference when a crest of one wave and a trough of another wave combine, thus canceling each other. A skilled artisan would, however, appreciate that there are many situations in which the interaction between the light waves is more complicated, e.g., when the light has a plurality of wavelengths.

The principles and operation of a waveguide, device and system according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention, there is provided a flexible waveguide 50 capable of propagating and emitting light.

Referring now to the drawings, FIG. 1 shows an exemplary and schematic illustration of waveguide 50, according to a preferred embodiment of the present invention. Waveguide 50 comprises a flexible material 52 having a surface 54 and an end 56. In use, when light 51 enters waveguide 50, a first portion 58 of light 51 is emitted through at least a portion of surface 54, while a second portion 60 of light 51 is emitted through end 56. Thus, waveguide 50 is capable of (i) transmitting light 51 through flexible material 52, (ii) emitting portion 58 of light 51 through surface 54, and (iii) emitting portion 60 of light 51 through end 56.

Flexible material 52 is preferably biocompatible, so as to allow implementation of waveguide 50 in medical applications. Additionally, flexible material 52 is preferably elastic, having elasticity of at least 100%, more preferably at least 300%, most preferably from 400% to 600%. Thus, flexible material 52 can be, for example, an elastomer.

Preferably, the material comprises a polymeric material. The polymeric material may optionally comprise a rubbery or rubber-like material. According to a preferred embodiment of the present invention flexible material 52 is preferably formed by dip-molding in a dipping medium, for example, a hydrocarbon solvent in which a rubbery material is dissolved or dispersed. The polymeric material optionally and preferably has a predetermined level of cross-linking, which is preferably between particular limits. The cross-linking may optionally be physical cross-linking, chemical cross-linking, or a combination thereof. A non-limiting illustrative example of a chemically cross-linked polymer comprises cross-linked polyisoprene rubber. A non-limiting illustrative example of a physically cross-linked polymer comprises cross-linked comprises block co-polymers or segmented co-polymers, which may be cross-linked due to micro-phase separation for example. Flexible material 52 is optionally cross-linked through application of a radiation selected from the group consisting of electron beam radiation and electromagnetic.

Although not limited to rubber itself, the material preferably has the physical characteristics of rubber, such as parameters relating to tensile strength and elasticity, which are well known in the art. For example, flexible material 52 is preferably characterized by a tensile set value which is below 5%. The tensile set value generally depends on the degree of cross-linking for cross-linked polymeric materials and is a measure of the ability of flexible material 52, after having been stretched either by inflation or by an externally applied force, to return to its original dimensions upon deflation or removal of the applied force.

The tensile set value can be determined, for example, by placing two reference marks on a strip of flexible material 52 and noting the distance between them along the strip, stretching the strip to a certain degree, for example, by increasing its elongation to 90% of its expected ultimate elongation, holding the stretch for a certain period of time, e.g., one minute, then releasing the strip and allowing it to return to its relaxed length, and re-measuring the distance between the two reference marks. The tensile set value is then determined by comparing the measurements before and after the stretch, subtracting one from the other, and dividing the difference by the measurement taken before the stretch. In this invention, using a stretch of about 90% of its expected ultimate elongation and a holding time of one minute, the preferred tensile set value is less than about 5%

The transmission of light 51 through flexible material 52 can be done in any way known in the art, such as, but not limited to, total internal reflection, graded refractive index and band gap optics. Additionally, polarized light may be used, in which case the propagation of light 51 can be facilitated by virtue of the reflective coefficient of flexible material 52. For example, a portion of flexible material can be made of a dielectric material having a sufficient reflective coefficient, so as to trap light 51 within at least a predetermined region of waveguide 50.

In any event, flexible material 52 is preferably designed and constructed such that at least a portion of light 51 propagates therethrough at a plurality of directions, so as to allow the emission of portion 58 through more than one point.

Figure 2:
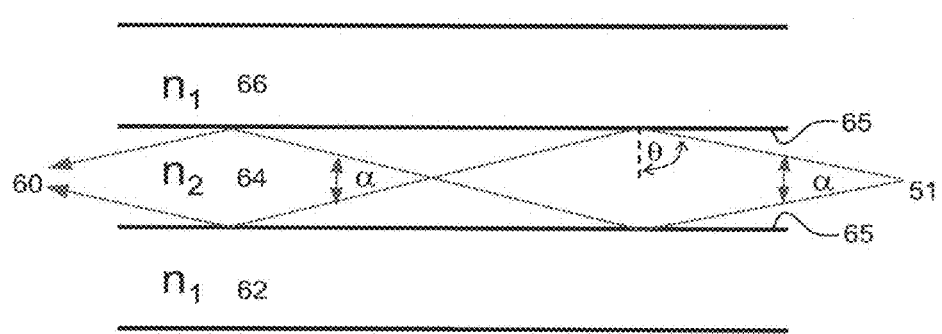
FIG. 2 is a schematic illustration of a flexible material in an embodiment in which three layers are employed.

Reference is now made to FIG. 2, which illustrates flexible material 52 in an embodiment in which total internal reflection is employed. Hence, in this embodiment flexible material 52 comprises a first layer 62, a second layer 64 and a third layer 66. Preferably, the refractive index of first 62 and third 66 layers, designated in FIG. 2 by $n_1$, is smaller than the refractive index, $n_2$, of second layer 64. In such configuration, when the light impinges on internal surfaces 65 of layer 64 at an impinging angle, $\theta$, which is larger than the critical angle, $\theta_c \equiv \sin^{-1}(n_1/n_2)$, the light energy is trapped within layer 64, and the light propagates therethrough in a predetermined propagation angle, $\alpha$. Subsequently, when portion 60 of light 51 arrives end 56 of flexible material 52, it exits into the surrounding medium.

It is to be understood that light 51 may propagate through waveguide 50 also when the impinging angle is smaller than the critical angle, in which case one portion of light 51 is emitted and the other portion thereof continue to propagate. For example, when flexible material 52 comprises dielectric or metallic materials, where the reflective coefficient depends on the impinging angle, $\theta$. This embodiment is particularly useful when light 51 is polarized, in which case flexible material 52 is preferably selected such that the reflective coefficient is sufficiently large so as to allow, as further detailed hereinabove.

The propagation angle, $\alpha$, which is approximately 90-$\theta$ (in degrees), depends on the thickness of flexible material 52 in general and each of first 62, second 64 and third layers 66. In addition, $\alpha$ depends on the ratio between the indices of refraction of the layers. Specifically, when $n_2$ is much larger than $n_1$, $\alpha$ is large, whereas when the ratio $n_2/n_1$ is close to, but above, unity, $\alpha$ is small. According to a preferred embodiment of the present invention the thickness of layers 62, 64 and 66 and the indices of refraction are selected such that light 51 propagates in a predetermined propagation angle. A typical thickness of each layer is from about 10 µm to about 3 mm, more preferably from about 50 µm to about 500 µm, most preferably from about 100 µm to about 200 µm.

The difference between the indices of refraction of layers 64 and 62 or between the indices of refraction of layers 64 and 62 is preferably selected in accordance with the desired propagation angle of light 51. According to a preferred embodiment of the present invention, the indices of refraction are selected such that propagation angle is from about 5 degrees to about 30 degrees. For example, layer 64 may be made of poly(cis-isoprene), having a refractive index of about 1.52, and layers 62 and 66 may be made of Poly(dimethyl siloxane) having a refractive index of about 1.45, so that $\Delta n = n_2 - n_1 \approx 0.07$ and $n_2/n_1 \approx 0.953$ corresponding to a propagation angle of about 17 degrees.

The emission of the light from the surface of flexible material 52 may be achieved in more than one way. Broadly speaking, one or more of layers 62, 64 and 66 preferably comprises at least one additional component 71 (not shown, see FIGS. 3a-d) designed and configured so as to allow the emission of the light through the surface. Following are several examples for the implementation of component 71, which are not intended to be limiting.

Figure 3A:
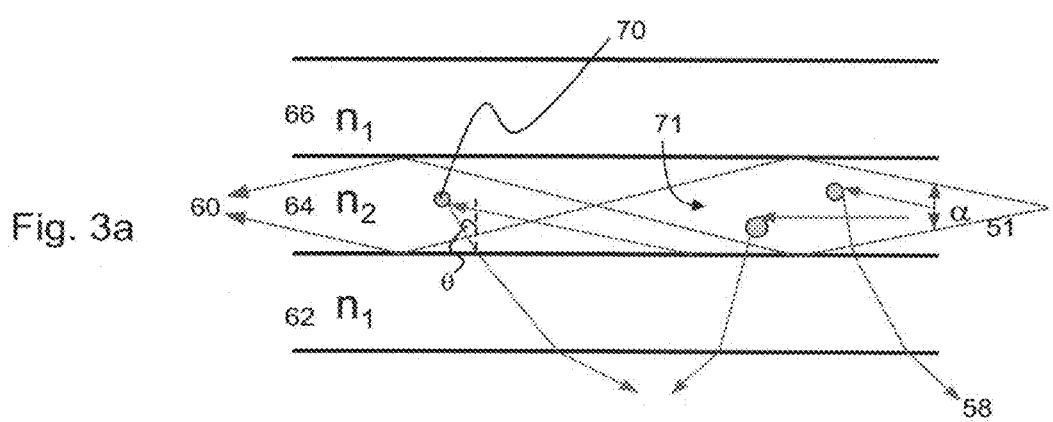
FIG. 3a is a schematic illustration of the flexible material in an embodiment in which at least one impurity is used for scattering a light.

Referring to FIG. 3a, in one embodiment, component 71 is implemented as at least one impurity 70, present in second layer 64 and capable of emitting first portion 58 of light 51, so as to change the propagation angle, $\alpha$, of the light. Impurity 70 may serve as a scatterer, which, as stated, can scatter radiation in more than one direction. When portion 58 is scattered by impurity 70 in such a direction that the impinging angle, $\theta$, which is below the above mentioned critical angle, $\theta_c$, no total internal reflection occurs and first portion 58 is emitted through surface 54 (not shown; see FIG. 1). According to a preferred embodiment of the present invention the concentration and distribution of impurity 70 is selected such that portion 58 of light 51 is emitted from a predetermined region of surface 54 (not shown; see FIG. 1). More specifically, in regions of waveguide 50 where larger portion of the propagated light is to be emitted through the surface, the concentration of impurity 70 is preferably large, while in regions where a small portion of the light 58 is to be emitted from surface 54 the concentration of impurity 70 is preferably smaller.

As will be appreciated by one ordinarily skilled in the art, the energy trapped in waveguide 50 decreases each time a light ray is emitted through surface 54. On the other hand, it is often desired to use waveguide 50 to provide a uniform surface illumination. Thus, as the overall amount of energy decreases with each emission, a uniform surface illumination can be achieved, either by gradually increasing the amount of light entering waveguide 50, or, alternatively and preferably, by gradually increasing the ratio between the emitted light and the propagated light. According to a preferred embodiment of the present invention, the increasing emitted/propagated ratio is achieved by an appropriate selection of the distribution of impurity 70 in layer 64. More specifically, the concentration of impurity 70 is preferably an increasing function of the optical distance which the propagated light travels.

Optionally, impurity 70 may comprise any object that scatters light and which is incorporated into the flexible materially, including but not limited to, beads, air bubbles, glass beads or other ceramic particles, rubber particles, silica particles and so forth, any of which may optionally be fluorescent particles or biological particles, such as, but not limited to, Lipids.

Figure 3B:
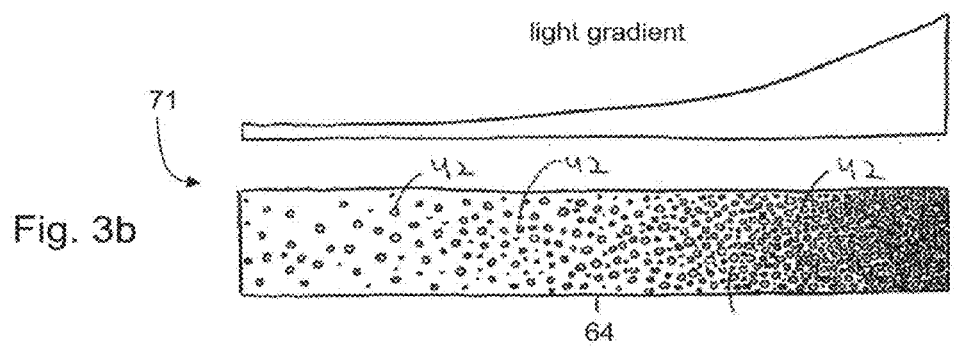
FIG. 3b is a schematic illustration of the flexible material in an embodiment in which the impurity is a plurality of particles, having a gradually increasing concentration.

FIG. 3b further details a preferred embodiment of the invention for a component 71. In FIG. 3b, impurity 70 is optionally and preferably implemented as a plurality of particles 42, distributed in an increasing concentration in layer 64 so as to provide a light gradient. Particles 42 are preferably organized so as to cause light to be transmitted with substantially lowered losses through scattering of the light. It should be noted that particles 42 may optionally be implemented as a plurality of bubbles in a solid plastic portion, such as a tube for example. According to a preferred embodiment of the present invention the size particles 42 is selected so as to selectively scatter a predetermined range of wavelengths of the light. More specifically small particles scatter small wavelengths and large particles scatter both small and large wavelengths. This embodiment is particularly useful in applications in which light 58 is used to carry information, as further detailed hereinunder, with reference to FIGS. 4a-c.

Particles 42 may also optionally act as filters, for example for filtering out particular wavelengths of light. Preferably, different types of particles 42 are used at different locations in waveguide 50. For example, particles 42 which are specific to scattering of a particular wavelength or a predetermined wavelength range may preferably be used within waveguide 50, at locations where such particular wavelength is to be emitted from waveguide 50 to provide illumination.

According to a preferred embodiment of the present invention impurity 70 is capable of producing different optical responses to different wavelengths of the light. The difference optical responses can be realized as different emission angles, different emission wavelengths and the like. For example, different emission wavelengths may be achieved by implementing impurity 70 as beads each having predetermined combination of color-components, e.g., a predetermined combination of fluorophore molecules.

When a fluorophore molecule embedded in a bead absorbs light, electrons are boosted to a higher energy shell of an unstable excited state. During the lifetime of excited state (typically 1-10 nanoseconds) the fluorochrome molecule undergoes conformational changes and is also subject to a multitude of possible interactions with its molecular environment. The energy of the excited state is partially dissipated, yielding a relaxed singlet excited state from which the excited electrons fall back to their stable ground state, emitting light of a specific wavelength. The emission spectrum is shifted towards a longer wavelength than its absorption spectrum. The difference in wavelength between the apex of the absorption and emission spectra of a fluorochrome (also referred to as the Stokes shift), is typically small.

Thus, in this embodiment, the wavelength (color) of the emitted light is controlled by the type(s) of fluorophore molecules embedded in the beads. Other objects having similar or other light emission properties may be also be used. Representative examples include, without limitation, fluorochromes, chromogenes, quantum dots, nanocrystals, nanoprisms, nanobarcodes, scattering metallic objects, resonance light scattering objects and solid prisms.

Referring to FIG. 3c, in another embodiment, component 71 is implemented as one or more diffractive optical elements 72 formed with layer 64, for at least partially diffracting the light. Thus, the propagated light, after a few reflections within layer 64, reaches optical element 72 where a portion of the light energy is coupled out of waveguide 50, while the remnant energy is redirected through an angle, which causes it to continue its propagation through layer 64.

When a plurality of optical elements 72 is used (two are exemplified in FIG. 3b), the process of partial refraction each optical element 72 is repeated during the propagation of the light (or, more precisely, the remnant thereof). The advantage of the presently preferred embodiment of the invention is that optical element 72 can be formed on a specific side of layer 64 so that only the respective external surface of flexible material 52 is capable of emitting the light while the other surface remains opaque.

Optical element 72 may be realized in many ways, including, without limitation, a non-smooth surface of layer 64, a mini-prism or grating formed on internal surface 65 and/or external surface 67 of layer 64. Diffraction Gratings are known to allow both redirection and transmission of light. The angle of redirection is determined by an appropriate choice of the period of the diffraction grating often called "the grating function." Furthermore, the diffraction efficiency controls the energy fraction that is transmitted at each strike of light on the grating. Hence, the diffraction efficiency may be predetermined so as to achieve an output having predefined light intensities; in particular, the diffraction efficiency may vary locally for providing substantially uniform light intensities. Optical element 70 may also be selected such that portion 58 of light 51 has a predetermined wavelength (i.e., color). For example, in the embodiment in which optical 70 is a diffraction grating, the grating function may be selected to allow diffraction of a predetermined range of wavelengths.

Referring to FIG. 3d, in an additional embodiment, one or more regions 74 of first layer 62 and/or second layer 66 may have different indices of refraction so as to prevent the light from being reflected from internal surface 65 of second layer 64. For example, denoting the index of refraction of region 74 by $n_3$, a skilled artisan would appreciate that when $n_3 > n_2$, no total internal reflection can take place, because the critical angle, $\theta_c$, is only defined when the ratio $n_3/n_2$ does not exceed the value of 1. An advantage of this embodiment is that the emission of portion 58 of light 51 through surface 54 is independent on the wavelength of the light. A representative example for the use of the presently preferred embodiment of the invention is by wetting one or more regions of layer 62 and/or 66 thereby increasing the index of refraction at the wetted region and allowing light 51 to exit.

Waveguide 50 of the present invention is capable of transmitting and emitting light both through its surface and through it end. The light may enter waveguide 50 for example, from any light source which is capable of providing electromagnetic radiation either in the visible range or in the non-visible range (e.g., the infrared range the ultraviolet range, etc.).

According to a preferred embodiment of the present invention, the light source may be connected to an optical fiber or a fiber bundle. The light source may be realized as an electric light source, for example an incandescent light source, a tungsten lamp, a xenon/neon lamp and/or any other type of halogen lamp, or a laser light source or other single or limited wavelength light source, such as, but not limited to, one or more light emitting diode (LEDs). Alternatively, the light source may be a chemical light source, for example a light stick.

According to a preferred embodiment of the present invention components 71 (e.g., impurity 70, optical element 72, region 74) allows portion 58 of light 51 to exit through surface 54 of waveguide 50 at a predetermined region. This embodiment is particularly useful in applications where the emitted light serves for carrying some kind of information. The information can be in any form which is suitable to be carried by light. For example, patterns (e.g., words, numbers, symbols), colors, intensities, etc.

Figure 4A:
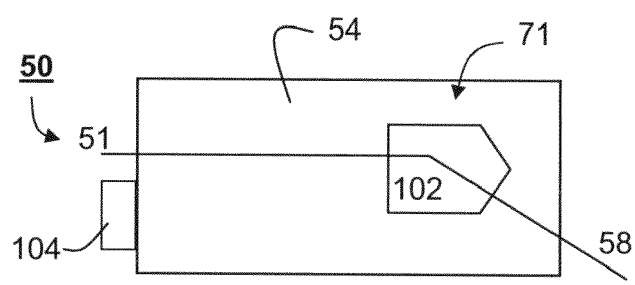
FIGS. 4a-b are schematic illustrations of the waveguide when used for providing information.
Figure 4B:
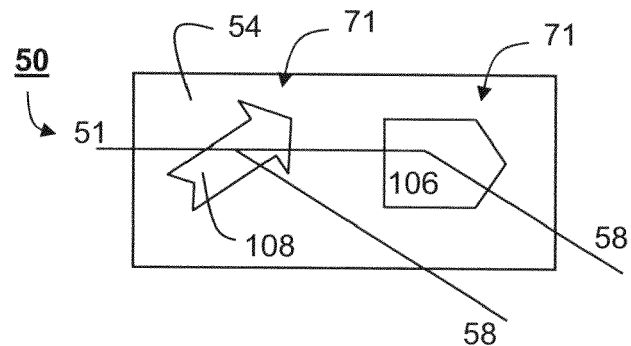

FIGS. 4a-b show different embodiments in which waveguide 50 provides information through component 71.

The simplest configuration is shown in FIG. 4a, arranged such that portion 58 exits through surface 54 in a particular pattern or patterns 102, so that when light 51 enters waveguide 50, pattern or patterns 102 are illuminated by portion 58 of light 51, hence providing the user with information in the form of the patterns which he observes. Consequently, when no light is present in waveguide 50, say, when the light source is switched off, for example by a switch 104, pattern or patterns 102 are not illuminated thereby provide the user with information in the form of the absence of patterns 102. This embodiment may be implemented using any of the above alternatives for component 71. More specifically pattern or patterns 102 may be defined by (i) an appropriate distribution of impurity 70; (ii) a judicious selection of the type and position of diffractive element 72; and (iii) an appropriate position of region 74.

Another embodiment, shown in FIG. 4b, is arranged such that when the incoming light 51 has a certain wavelength (color), light 58 exits in one pattern or patterns 106 and when light 51 has another wavelength portion 58 of light 51 exits in a different pattern or patterns 108. Thus, in this embodiment, waveguide 50 displays different patterns for different wavelengths of the incoming light (light 51). This embodiment is preferably implemented in combination with the embodiment in which impurity 70 is capable of producing different emission wavelengths to different wavelengths of the incoming light, as further detailed hereinabove.

In an additional embodiment, the intensity or the color of light 58 provides the necessary information. For example, a change in the color of light 58 and/or a change in the intensity thereof, provides the user with information of a change in temperature, moisture, electromagnetic field, etc., in the proximity of waveguide 50. This embodiment is preferably implemented in combination in embodiment in which component 71 is sensitive to temperature, moisture, or electromagnetic field. For example, in this embodiment, component 71 may comprise a dielectric or metallic material, in which case the reflection and refraction properties of flexible material 52 are sensitive to environmental conditions such as, but not limited to, temperature and electromagnetic field. Alternatively, component 71 may include any of the above alternatives, in which case the refraction indices of layers 62 and/or 66 preferably depend on the level of moisture in the air.

The present invention successfully provides an optical coupler for directing the light from the light source into a waveguide (e.g., waveguide 50), an optical fiber or a fiber bundle, for the purpose of trapping the light within the waveguide.

In one embodiment, the optical coupler may be realized as a solid state device into which light enters at a predetermined angle and exits at a plurality of angles, such that each portion of the waveguide or each optical fiber in the fiber bundle is engaged by a portion of the light. One would appreciate that this could be done either for a coherent light or for a multi-wavelength light. Alternatively, the optical coupler may optionally split the light according to its wavelength, thereby directing different wavelengths to different directions. This embodiment may be used, e.g., in applications in which it is desired that different portions of the waveguide or different fibers in the fiber bundle provide light of different colors.

Figure 5A:
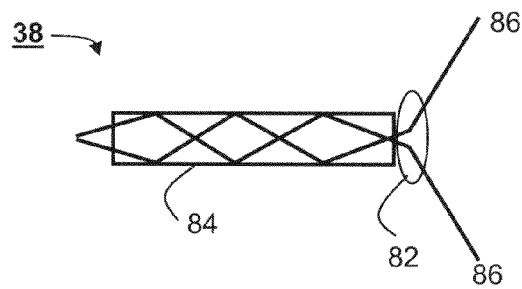
FIGS. 5a-d are schematic illustrations of optical coupler, according to a preferred embodiment of the present invention.

Reference is now made to FIG. 5a, which is a schematic illustration of an exemplary optical coupler, according to a preferred embodiment of the present invention. The optical coupler comprises a converging optical element 82 and a waveguide 84. Converging optical element 82 can be, for example a light transmissive substrate having a spherical or any other geometrical shape which is suitable for converging the light beam to its focal point. Waveguide 84 may be, for example, an optical fiber, an optical fiber bundle, a flexible material (such as, but not limited to, flexible material 52) and the like.

As stated, any light transmitting optical system can be characterized by a parameter known as the numerical aperture, which is commonly defined as the sine of the largest incident light ray angle that is successfully transmitted therethrough, multiplied by the index of refraction of the medium from which the light ray enters the optical system. Thus, according to a preferred embodiment of the present invention optical element 82 is capable of focusing a light beam to impinge on waveguide 84 at an impinging angle satisfying the numerical aperture which characterizes waveguide 84. The light beam is represented in FIG. 5a by its outermost light rays 86.

Figure 5B:
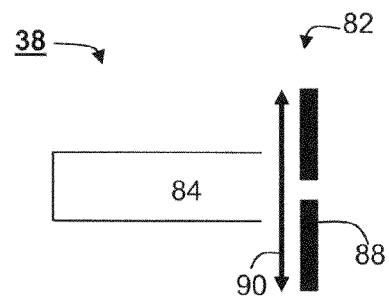

Referring to FIG. 5b, in one configuration, optical element 82 comprises a converging lens 90 (e.g., a microlens) and a shutter 88. Converging lens 90 serves for focusing the light into waveguide 84, and shutter 88 serves for blocking any light ray which cannot satisfy the numerical aperture of waveguide 84. When the light beam emanating from the light source is substantially narrow, shutter 88 may be excluded from optical element 82.

The focal distance, f of a lens of radius, r, having a refractive index, n, satisfy the following equation:

$$f^{-1}=(n-1)r^{-1}. \qquad (\text{Eq. 1})$$

Figure 5C:
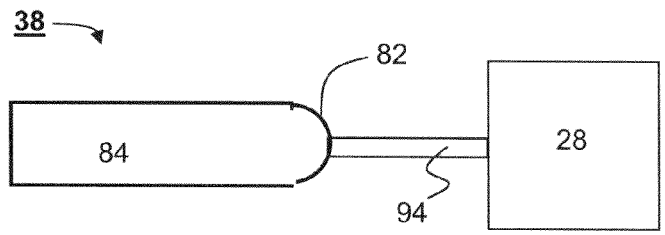

As a representative numerical example, supposing that the refractive index of waveguide 84 is about 1.5, then, the focal distance of lens 90, which satisfies Equation 1, approximately equals its radius. Referring now to FIG. 5c, if, for example, light source 28 is connected to an optical fiber or a fiber bundle 94, lens 90 is can be embodied as a curvature of waveguide 84, thus collecting a substantial portion of the light from light source 28. This embodiment is particularly useful when the diameter of optical fiber 94 (or each optical fiber if a fiber bundle is used) is of the order of the thickness of waveguide 84.

Figure 5D:
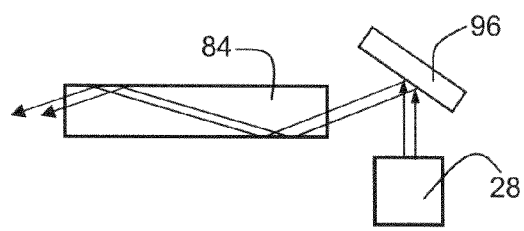

Referring now to FIG. 5d, when light source 28 is not coupled to an optical fiber, optical element may be realized as a reflector 96 (e.g., a converging reflector) which serve for redirecting the light into waveguide 84. This embodiment is particularly useful when light source 28 is sufficiently small to be positioned in close proximity to waveguide 84 and reflector 96. For example, this embodiment may be employed when the light source comprises a LED or a compact chemical light source (such as, but not limited to, a light stick). Reflector 96 may also be combined with shutter 88 (not shown). In this embodiment, a portion of the light which is reflected by reflector 96 and which does not satisfy the numerical aperture of waveguide 84 is blocked by shutter 88.

As stated, flexible material 52 preferably comprises polymeric material. The polymeric material may optionally comprise natural rubber, a synthetic rubber or a combination thereof. For example, latex may optionally be used. Examples of synthetic rubbers, particularly those which are suitable for medical articles and devices, are taught in U.S. Pat. No. 6,329,444, hereby incorporated by reference as if fully set forth herein with regard to such illustrative, non-limiting examples. The synthetic rubber in this patent is prepared from cis-1,4-polyisoprene, although of course other synthetic rubbers could optionally be used. Natural rubber may optionally be obtained from *Hevena brasiliensis* or any other suitable species.

Other exemplary materials, which may optionally be used alone or in combination with each other, or with one or more of the above rubber materials, include but are not limited to, crosslinked polymers such as: polyolefins, including but not limited to, polyisoprene, polybutadiene, ethylene-propylene copolymers, chlorinated olefins such as polychloroprene (neoprene) block copolymers, including diblock-, triblock-, multiblock- or star-block-, such as: styrene-butadiene-styrene copolymers, or styrene-isoprene-styrene copolymers (preferably with styrene content from about 1% to about 37%), segmented copolymers such as polyurethanes, polyether-urethanes, segmented polyether copolymers, silicone polymers, including copolymers, and fluorinated polymers and copolymers. Other exemplary materials include but are not limited to, polyvinylchloride, nitrile, poly(2,3-dimethylbutadiene), poly(dimethyl siloxane), ethylene/vinyl acetate copolymer-40% vinyl acetate, ethylene/vinyl acetate copolymer-30% vinyl acetate, poly(butadiene-co-acrylonitrile), optionally with one or more additives (e.g., colloidal silica).

For example, optionally and preferably, the second layer comprises polyisoprene, while the first layer optionally and preferably comprises silicone. If a third layer is present, it also optionally and preferably comprises silicone.

According to an optional embodiment of the present invention, the flexible material is formed by dip-molding in a dipping medium. Optionally, the dipping medium comprises a hydrocarbon solvent in which a rubbery material is dissolved or dispersed. Also optionally, the dipping medium may comprise one or more additives selected from the group consisting of cure accelerators, sensitizers, activators, emulsifying agents, cross-linking agents, plasticizers, antioxidants and reinforcing agents.

Coupler 38 and/or waveguide 50 may be used in many applications, such as, but not limited to, in a clothing device. According to a preferred embodiment of the present invention reflector 96, light source 28, and/or shutter 88 are shaped in accordance with the application for which they are used. For example, coupler 38 and/or waveguide 50 may be implemented in a glove device, in which case reflector 96, light source 28 and/or shutter 88 are shaped as a ring, compatible with the hand of the user.

The clothing device of the present invention is preferably naturally worn for many different types of manual procedures. For example, in one embodiment, the device and system of the present invention implemented as gloves which may be worn is in order to protect the individual performing the procedure and/or the environment in which the procedure is being performed.

Illustrative examples of such environments and/or procedures for using the present invention include, but are not limited to, medical environments and/or procedures, including those located in a hospital or other controlled medical setting, and those performed in such non or less controlled settings as battlefields and other military environments, and/or pre-hospital situations, and/or industrial environments; "clean rooms" for the production of specialized electronic equipment; law enforcement situations; and scientific and/or research environments.

Additionally, the clothing can be used as an identification device in which the individual who wears the clothing is identified by the wavelength of the light emitted thereby. Further, the clothing can be used as a selective identification device, for example, when the wavelength of the emitted light is in the invisible range (e.g., infrared or ultraviolet) so that the individual who wears the clothing, according to a preferred embodiment of the present invention, can only be identified by an armed eye.

The clothing may optionally and preferably be constructed of such materials as latex, rubber, or any synthetic plastic material, such as any type of plastic polymer such as vinyl, nitrile, or any other suitable material, or a combination thereof. Preferably, the clothing or at least a portion thereof is manufactured from flexible material 52 so as to facilitate the propagation and emission of light, as further detailed hereinabove.

The clothing according to the present invention optionally and preferably include a light source connected to the clothing itself, for example through fiber optics. The light source may optionally be located at a distance from the clothing, for example as a "belt pack" or other portable system for being carried on the body of the person wearing the clothing. The "belt pack" or other container system may also optionally hold the energy source for the light source. Alternatively, the light source may optionally be attached directly to the clothing. In any event, the clothing preferably also features waveguides, e.g., waveguide 50. More preferably, the waveguide is attached to or embedded within the material of the clothing. Alternatively the waveguide can be prepared as a separate external layer to the clothing. This material can also optionally be blended, for example as a chemical substance added to the latex blend, such as polystyrene, rather than as a plurality of sliced fiber optic pieces. These waveguides preferably include material for directing the light to a particular point or multiple points, in order to avoid absorption of the light through the fiber optic material before it reaches the desired location. For example, if waveguide 50 is used, light propagates therethrough and being emitted, inter alia, through the surface thereof, as further detailed hereinabove.

Alternatively, the fiber optic material may optionally be provided as a fiber optic and/or a bundle of fiber optics.

Also, optionally and more preferably, the light is transmitted from various points in the clothing. Such points may optionally be constructed from small fiber optic parts and/or a different polymeric material such as polystyrene for example. Alternatively, if waveguide 50 is used such points may be inherent to the construction thereof.

For example, when clothing is implemented as gloves, the light may be selectively transmitted from the tips of one or more fingers. More preferably, when the gloves are warn, for example, by a surgeon, the light is only transmitted from the underside (palm side) of the gloves, in order to avoid light being transmitted to the eyes of the surgeon, thereby causing glare.

Optionally and more preferably, a plurality of individuals using the clothing for collectively performing the process may wear different types of clothing. For example, a surgeon may optionally choose to wear gloves with illumination at the tips, while a nurse may optionally wear gloves providing illumination over a large portion of the area of the hand.

Figure 6:
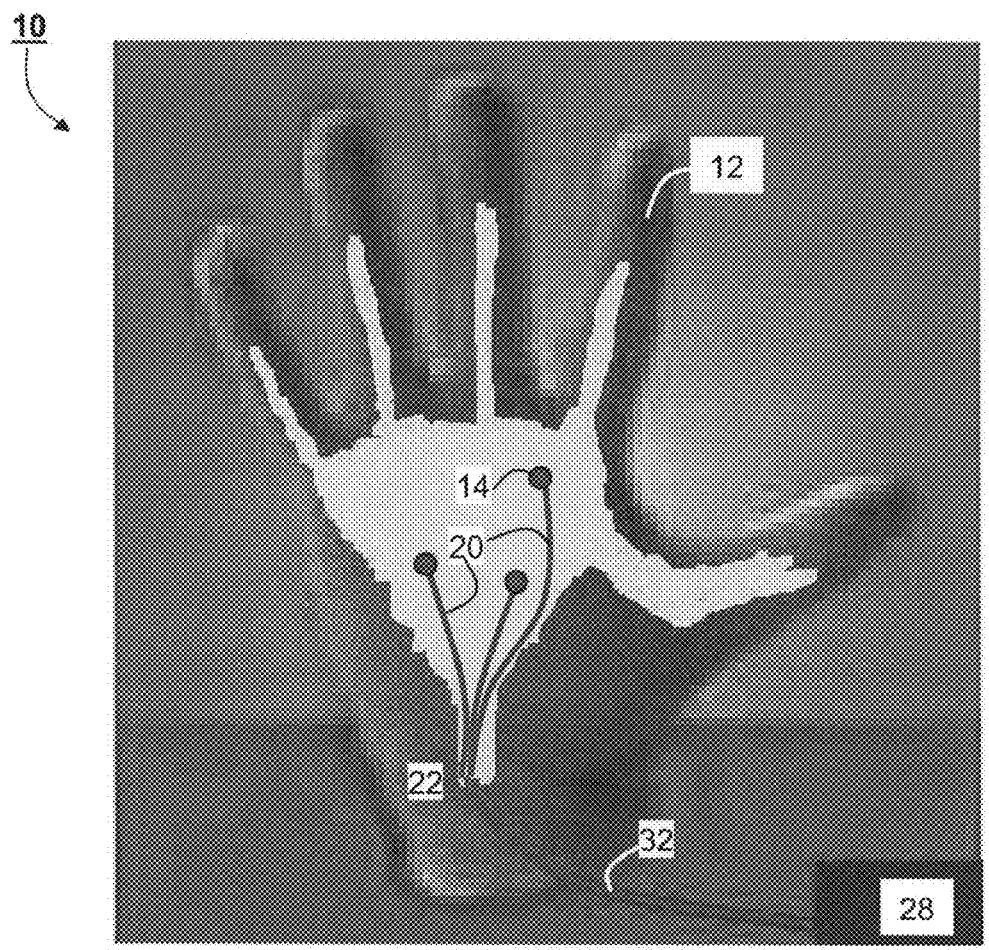
FIG. 6 shows a schematic implementation of a glove device according to the present invention.

Referring now again to the drawings, FIG. 6 shows an exemplary and schematic implementation of a clothing device 10 according to the present invention. For illustrative purpose only, clothing device 10 is shown as a glove device, which includes a glove 12. It is to be understood that clothing device 10 may be implemented in any other clothing, such as, but not limited to, sleeves, hats and socks, which are naturally worn for many different types of manual procedures.

Hence, as shown in FIG. 6, device 10 preferably features a glove 12 for covering at least a portion of a human hand. Glove 12 may optionally be constructed of latex, rubber, or any synthetic plastic material, such as any type of plastic polymer such as vinyl, or a combination thereof. Different types of each of these materials may also optionally be used, such as thermoplastic and/or vulcanized rubber, for example. Examples of plastic polymers include but are not limited to, PVC, PVP and polystyrene. Preferably, any type of suitable material that may be used for gloves of the type desired for a particular implementation of the present invention, as is known in the art. Furthermore, such glove material is more preferably in compliance with international standards regarding ageing and heat resistance, as described for example in the standard ISO 188 (reference number ISO 188:1998 (E)), hereby incorporated by reference as if fully set forth herein.

Optionally and preferably glove 12 features a plurality of light transmission points 14, through which the light is provided for illumination. For the optional and preferred implementation of the present invention with fiber optics, light is preferably channeled to light transmission points 14 through at least one optical fiber 20. Optical fiber 20 may optionally be constructed according to any well known method in the art. Alternatively or in addition, glove 12 preferably features waveguide 50 so that light propagates through and emitted from waveguide 50, as further detailed hereinabove, with reference to FIGS. 1-3.

Optical fiber 20 preferably receives light from a light source 28. Although such a light source may optionally be mounted on glove 12, more preferably, light is transmitted from the light source through one or more optical fibers 32 through a connector 22, which connects these one or more optical fibers to optical fibers 20, or to waveguide 50.

The light source is optionally and preferably capable of generating illumination suitable for the particular application for which glove 12 is used. For example, if glove 12 is worn by a surgeon in an operating room, the light source preferably generates at least 150-foot candles, which is the preferred illumination flux on the operation table.

Figure 7A:
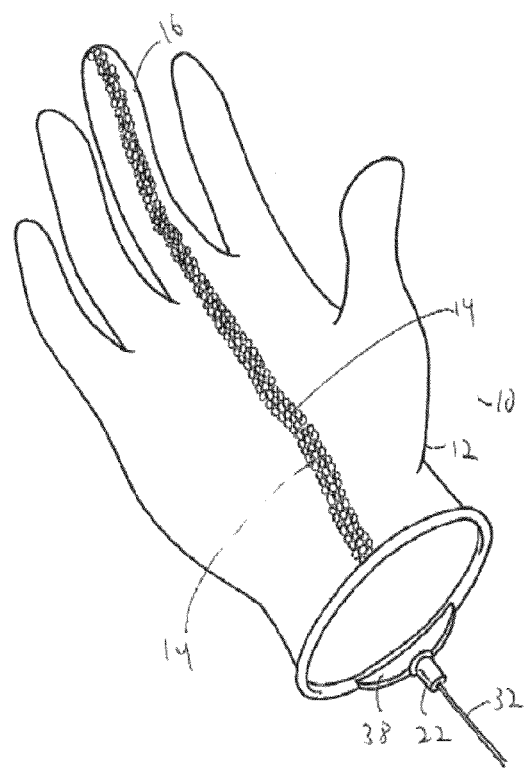
FIGS. 7a and 7b show exemplary implementations of a glove device according to the present invention.
Figure 7B:
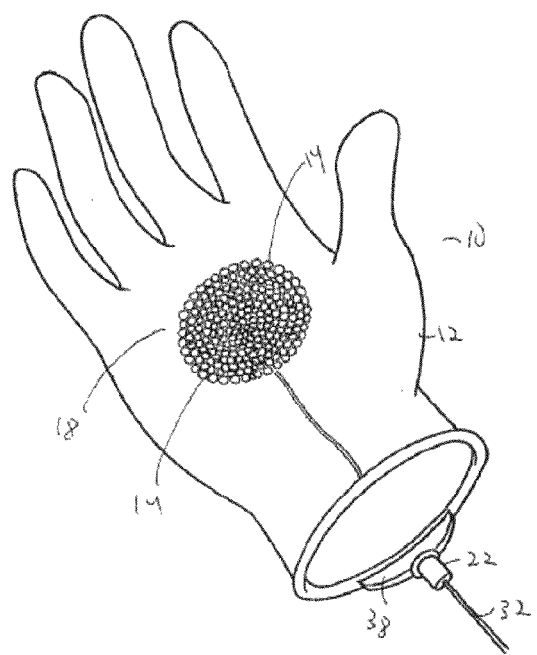

As shown in FIGS. 7a and 7b, optionally and preferably glove 12 features a plurality of light transmission points 14. Such light transmission points may be constructed, as stated, either using a plurality of optical fibers 20 (not shown) or by a proper design of waveguide 50 (for example, by a judicious distribution of impurity 70, optical element 72 or regions 74 as further detailed hereinabove with regard to FIGS. 3a-c). According to a preferred embodiment of the present invention, at least a portion of light transmission points 14 are present in at least one fingertip 16 of glove 12, as shown in FIG. 7a. The implementation of light transmission points 14 in FIG. 7a is one option, with light transmission points 14 arranged in a band or line.

As shown in FIG. 7b, alternatively and optionally, a portion of light transmission points 14 may be present at another location of glove 12, such as at palm 18 of glove 12. Optionally and more preferably, different types of gloves 12 may have light transmission points 14 at different locations and/or may predominantly have light transmission points 14 at particular locations, such as fingertip 16 as opposed to palm 18, for example.

Figure 8A:
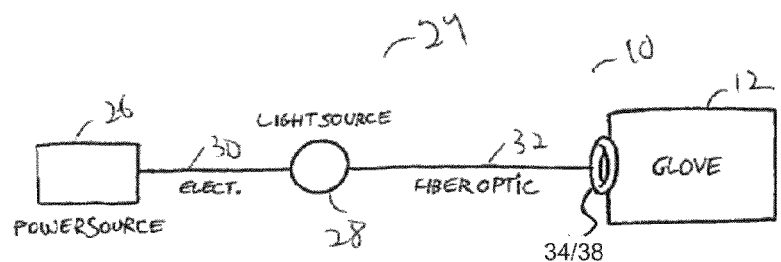
FIGS. 8a and 8b show schematic block diagrams of two different exemplary implementations of a system according to the present invention.
Figure 8B:
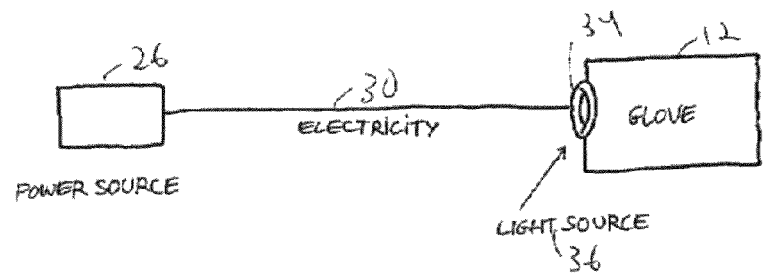

FIGS. 8a and 8b show two different exemplary implementations of a system 24 for providing light for transmission to glove device 10, as schematic block diagrams. FIG. 8a shows a first preferred implementation of system 24, in which a power source 26 provides power to a light source 28. Such power may optionally be provided through an electrical connector 30, for example.

Light source 28 is located separately from glove device 10, and may be located at any convenient location, for example attached to a belt pack for being worn by the user (not shown). An optical fiber 32 preferably transmits light from light source 28 to glove device 10. Optionally and more preferably, optical fiber 32 transmits such light to a ring connector 34 or an optical coupler 38 mounted on glove device 10. Ring connector 34 may supports optical fibers 20 when such optical fibers are employed, for actually transmitting the light throughout glove device 10.

Optical fiber 32 is preferably connected to light source 28 in a manner that light from light source 28 impinges on optical fiber 32 in accordance with the numerical aperture of optical fiber 32. In addition, optical fiber 32 and ring connector 34 or optical coupler 38 are preferably connected, such that the light being transmitted from optical fiber 32 to ring connector 34 is directed in accordance with the numerical aperture of each of optical fibers 20, or waveguide 50. Ring connector 34 may also optionally feature particles (not shown) for reflecting the light to the proper location within glove device 12, as described in greater detail with regard to FIG. 9.

As shown in FIG. 8b, system 24 also features power source 26, glove device 10 and electrical connector 30. However, for this alternative implementation, a light source 36 is preferably mounted on glove device 10, for example at ring connector 34.

For either embodiment, substantially any type of light source may optionally be used, including but not limited to, an incandescent light source, a tungsten lamp, a xenon/neon lamp and/or any other type of halogen lamp, or a laser light source or other single or limited wavelength light source.

Figure 9:
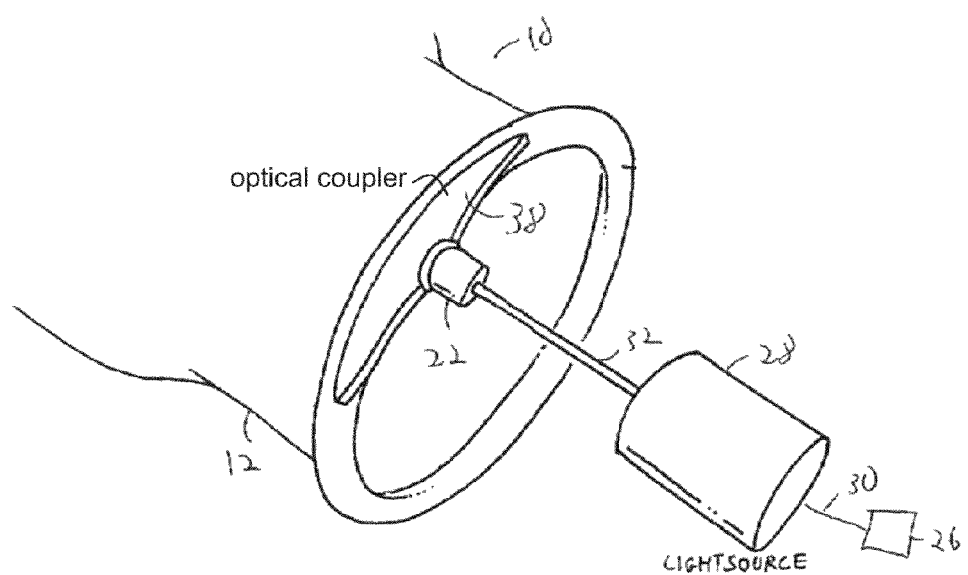
FIG. 9 is a schematic illustration of a portion of the system of FIGS. 8a and 8b, in an embodiment in which a light source is located at a physical distance from the glove device.

FIG. 9 shows a portion of system 24, according to the preferred embodiment in which light source 28 is located at a physical distance from glove device 10. As shown, energy source 26 provides energy to light source 28 through electrical connector 30. Light is then transmitted from light source 28 through optical fiber (or fiber bundle) 32 to glove device 10, only a portion of which is shown. Preferably, optical fiber 32 connects to glove device 10 at connector 22. A plurality of connectors 22 may optionally be used to form ring connector 34 (not shown, see FIGS. 8a and 8b). Connector 22 preferably then connects to an optical coupler 38. Optical coupler 38 is preferably connected to optical fibers (not shown), such that light is transmitted through the optical fibers. Alternatively, rather than using optical fibers, light could optionally be channeled through glove device 10 with waveguide 50 as further detailed hereinabove.

Figure 10:
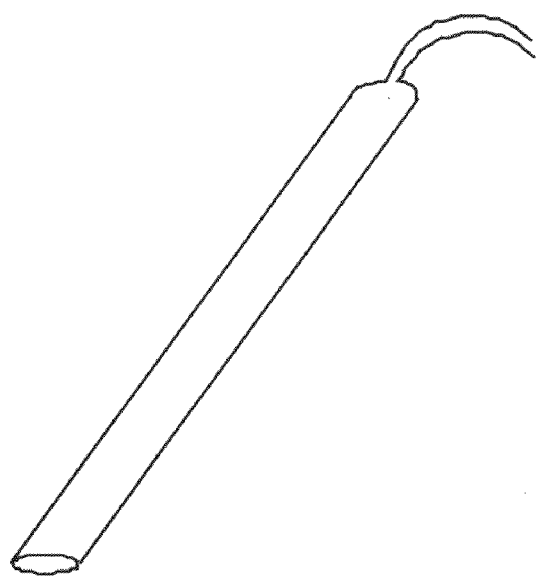
FIG. 10 shows an exemplary cannula according to the present invention.
Figure 11:
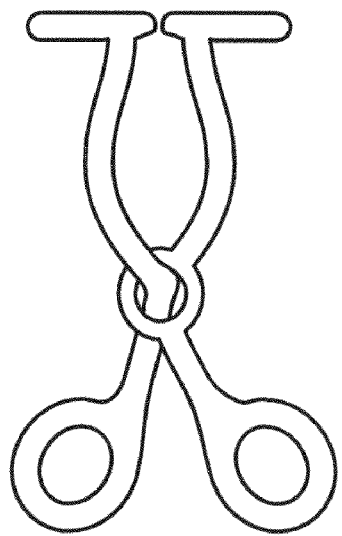
FIG. 11 shows an exemplary surgical clamp according to the present invention.

Other types of devices may optionally be used in place of clothing for the present invention, such as a cannula (shown in FIG. 10) and/or surgical clamps (shown in FIG. 11). Each of these devices is characterized by being at least partially constructable from clear or translucent plastic, thereby permitting the transmission of light therefrom. Preferably, at least a portion of each of these devices is made of a flexible material, such as, but not limited to, flexible material 52, which is capable of transmitting and emitting light, as further detailed hereinabove.

It is expected that during the life of this patent many relevant light transmitting optical systems will be developed and the scope of the term optical fiber is intended to include all such new technologies a priori.

As used herein the term "about" refers to ±10%.

Additional objects, advantages and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLES

Reference is now made to the following examples, which, together with the above descriptions, illustrate the invention in a non limiting fashion.

Example 1

Flexible Materials and Indices of Refraction

Representative examples for polymers which may be used for any of layers 62, 64 and 66 include, without limitations, Latex, with index of refraction of 1.514; polyvinylchloride, with index of refraction of 1.539; Nitrile, with index of refraction of about 1.52; and Chloroprene (Neoprene), with index of refraction of 1.558. Other materials which may be used include, without limitation, poly(cis-isoprene), with index of refraction of 1.5191; Poly(2,3-dimethylbutadiene), with index of refraction of 1.525; Poly(dimethyl siloxane), with index of refraction of 1.4035; Ethylene/vinyl acetate copolymer-40% vinyl acetate, with index of refraction of 1.4760; Ethylene/vinyl acetate copolymer-30% vinyl acetate, with index of refraction of 1.4820, Poly(butadiene-co-acrylonitrile), with index of refraction of 1.52; natural rubber, with index of refraction of 1.514; and Poly(chloroprene), with index of refraction of 1.558. In addition, a high refractive index may also be achieved, in accordance with optional preferred embodiment of the present invention, by using additives (e.g., colloidal silica).

Example 2

Prototype Waveguide

A prototype waveguide was manufactured, according to a preferred embodiment of the present invention. Specifically, the prototype waveguide included three layers (see FIG. 2), in which an intermediate layer (layer 64 in FIG. 2) served as the core waveguide and the external layers (layers 62 and 66 in FIG. 2) served as the clad. The intermediate layer was made of polyisoprene having a refractive index $n_2 \approx 1.52$, and each of the external layers was made of silicone rubber, having a refractive index $n_1 \approx 1.40$.

Polyisoprene and silicone rubber are biocompatible polymers which are commonly used in many medical devices, for example gloves. These materials have proven to be highly transparent to visible light, hence were suitable to serve as a core material for the prototype waveguide. When crosslinked both materials exhibit elasticity of about 500%, which is suitable for medical gloves.

Figure 12:
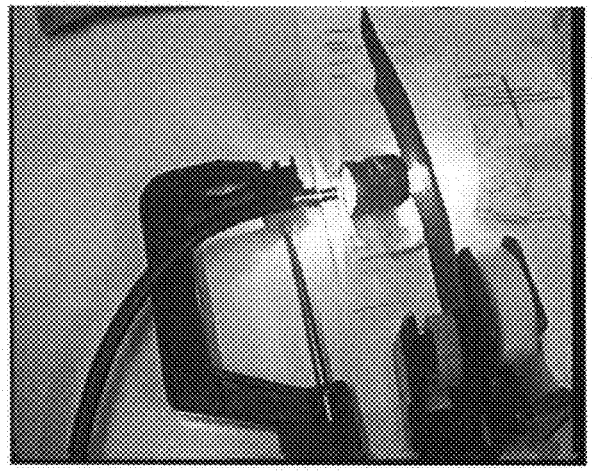
FIG. 12 shows coupling between a light source and a prototype waveguide.

FIG. 12 shows the coupling between the light source and the prototype waveguide. As shown, the light successfully channeled into the waveguide.

Figure 13A:
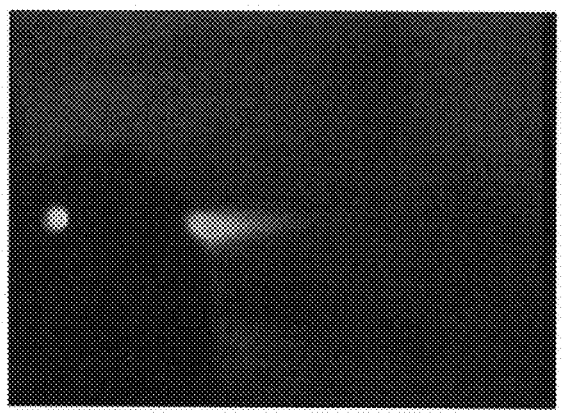
FIGS. 13a-c show illumination provided by the prototype waveguide at three different levels of light intensities: low (FIG. 13a), medium (FIG. 13b) and high (FIG. 13c).
Figure 13B:
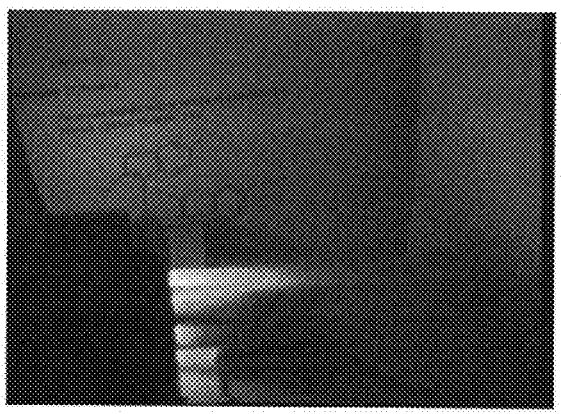
Figure 13C:
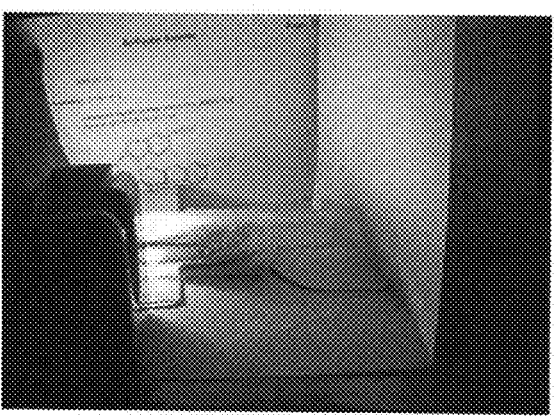

FIGS. 13a-c show the illumination provided by the prototype waveguide at three different levels of light intensities: low (FIG. 13a), medium (FIG. 13b) and high (FIG. 13c). As shown the prototype waveguide is capable of transmitting light therethrough, whereby a portion of the light is emitted through its surface. A sample located near the prototype waveguide is clearly illuminated thereby.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A waveguide for propagating and emitting light, the waveguide being shaped as a sheet and comprising a first layer of waveguide material shaped as a sheet and second layer of waveguide material shaped as a sheet, said first layer and said second layers being mutually overlapping,
   wherein said first layer is configured such that a first light portion propagates in said first layer and a second light portion passes into said second layer,
   wherein said second layer comprises particles which comprise at least one object or substance selected from the group consisting of fluorophores, fluorochromes and chromogenes, and
   wherein at least part of said second light portion exits out of the waveguide through an external surface of said second layer opposite to said first layer.

2. The waveguide of claim 1, further comprising an additional layer interposed between said first layer and said second layer.

3. The waveguide of claim 1, further comprising an optical element at an interface between said first layer and said second layer, said optical element selectively allows light transmission therethrough.

4. The waveguide of claim 1, further comprising an optical element at an interface between said first layer and said second layer, for partially transmitting and partially reflecting light impinging on said interface.

5. The waveguide of claim 3, wherein said optical element produces different optical responses to different wavelengths of the light.

6. The waveguide of claim 5, wherein said different optical responses comprises different emission angles.

7. The waveguide of claim 5, wherein said different optical responses comprises different emission wavelengths.

8. The waveguide of claim 3, wherein said optical element produces different optical responses to different incidence angles of the light.

9. The waveguide of claim 8, wherein said different optical responses comprises different emission angles.

10. The waveguide of claim 8, wherein said different optical responses comprises different emission wavelengths.

11. The waveguide of claim 3, wherein said optical element comprises a diffractive optical element.

12. The waveguide of claim 3, wherein said optical element is a non-smooth surface of at least one of said layers at said interface.

13. The waveguide of claim 3, wherein said optical element is a diffraction grating.

14. The waveguide of claim 2, further comprising an optical element at an interface between said additional layer and said first layer, said optical element selectively allows light transmission therethrough.

15. The waveguide of claim 2, further comprising an optical element at an interface between said additional layer and said first layer, for partially transmitting and partially reflecting light impinging on said interface.

16. The waveguide of claim 14, wherein said optical element produces different optical responses to different wavelengths of the light.

17. The waveguide of claim 16, wherein said different optical responses comprises different emission angles.

18. The waveguide of claim 16, wherein said different optical responses comprises different emission wavelengths.

19. The waveguide of claim 14, wherein said optical element produces different optical responses to different incidence angles of the light.

20. The waveguide of claim 19, wherein said different optical responses comprises different emission angles.

21. The waveguide of claim 19, wherein said different optical responses comprises different emission wavelengths.

22. The waveguide of claim 14, wherein said optical element comprises a diffractive optical element.

23. The waveguide of claim 14, wherein said optical element is a non-smooth surface of at least one of said layers at said interface.

24. The waveguide of claim 14, wherein said optical element is a diffraction grating.

25. The waveguide of claim 1, wherein particles within at least one of said first and said second layer are distributed in said layer in an increasing concentration such that a portion of the light is scattered by said particles and emitted through a surface of said sheet to provide a generally uniform surface illumination.

26. The waveguide of claim 1, wherein at least one of said layers is made of a waveguide material which is flexible.

27. The waveguide of claim 1, wherein at least one of said layers is made of a waveguide material which is elastic.

28. The waveguide of claim 27, wherein said elastic waveguide material is characterized by an elasticity of at least 100%.

29. The waveguide of claim 27, wherein said elastic waveguide material is characterized by tensile set value of less than about 5%.

30. The waveguide of claim 1, wherein at least one of said layers is made of a waveguide material which comprises a dielectric material, and wherein a reflection coefficient of said dielectric material is selected so as to allow propagation of polarized light through the waveguide, and emission of said polarized light through said surface.

31. The waveguide of claim 1, wherein the light is emitted through said surface along a predetermined pattern.

32. A method of relaying light, comprising:
   coupling light into a waveguide shaped as a sheet such that that the light propagates in said sheet and is emitted through a surface of said sheet;
   wherein said waveguide comprises a first layer of waveguide material shaped as a sheet and second layer of waveguide material shaped as a sheet, said first layer and said second layers being mutually overlapping,
   wherein said first layer is configured such that at least a portion of the light propagates in said first layer and at least a portion of the light passes into said second layer,
   wherein said second layer has particles which comprise at least one object or substance selected from the group consisting of fluorophores, fluorochromes and chromogenes, and
   wherein at least part of said second light portion exits out of the waveguide through an external surface of said second layer opposite to said first layer.

33. The method of claim 32, further comprising selectively allowing light transmission from said first layer to said second layer, using an optical element at an interface between said first layer and said second layer.

34. The method of claim 32, wherein said first light portion propagates, at least in part, via total internal reflection within said first layer.

35. The method of claim 32, wherein at least one of said first layer and said second layer comprises at least one object selected from the group consisting of quantum dots, nanocrystals, nanoprisms and nanobarcodes.

36. The method of claim 32, wherein at least one of said first layer and said second layer comprises at least one object selected from the group consisting of scattering metallic objects, resonance light scattering objects and solid prisms.

37. The waveguide of claim 1, wherein said first layer comprises a plurality of particles for scattering said second light portion to enter said second layer.

38. The waveguide of claim 1, wherein said first light portion propagates, at least in part, via total internal reflection within said first layer.

39. The waveguide of claim 1, wherein at least one of said first layer and said second layer comprises at least one object selected from the group consisting of quantum dots, nanocrystals, nanoprisms and nanobarcodes.

40. The waveguide of claim 1, wherein at least one of said first layer and said second layer comprises at least one object selected from the group consisting of scattering metallic objects, resonance light scattering objects and solid prisms.

* * * * *